(12) United States Patent
Layton et al.

(10) Patent No.: US 8,481,503 B2
(45) Date of Patent: Jul. 9, 2013

(54) COMBINATION CANCER THERAPY WITH AN AKT INHIBITOR AND OTHER ANTICANCER AGENTS

(75) Inventors: Mark E. Layton, Harleysville, PA (US); Hiroshi Hirai, Tsukuba (JP); Hidehito Kotani, Tsukuba (JP)

(73) Assignees: Merck Sharp & Dohme Corp., Rahway, NJ (US); MSD K.K., Chiyoda-Ku, Tokyo (JP)

( * ) Notice: Subject to any disclaimer, the term of this patent is extended or adjusted under 35 U.S.C. 154(b) by 28 days.

(21) Appl. No.: 13/254,108

(22) PCT Filed: Feb. 23, 2010

(86) PCT No.: PCT/US2010/025028
§ 371 (c)(1),
(2), (4) Date: Aug. 31, 2011

(87) PCT Pub. No.: WO2010/101734
PCT Pub. Date: Sep. 10, 2010

(65) Prior Publication Data
US 2011/0319354 A1 Dec. 29, 2011

Related U.S. Application Data

(60) Provisional application No. 61/158,109, filed on Mar. 6, 2009.

(51) Int. Cl.
*A01N 43/04* (2006.01)
*A61K 31/70* (2006.01)

(52) U.S. Cl.
USPC .................. 514/43; 514/42; 514/49; 514/50

(58) Field of Classification Search
None
See application file for complete search history.

(56) References Cited

U.S. PATENT DOCUMENTS

2008/0161317 A1 * 7/2008 Kelly et al. .................. 514/250

* cited by examiner

*Primary Examiner* — Patrick Lewis
(74) *Attorney, Agent, or Firm* — Yong Zhao; David A. Muthard; Matthew A. Leff

(57) ABSTRACT

The invention relates to combination anticancer therapy with certain Akt inhibitor and other anticancer agents such as anticancer antimetabolites, anticancer antibiotics, plant-derived anticancer agents, anticancer platinum-coordinated complex compounds, anticancer camptothecin derivatives and anticancer tyrosine kinase inhibitors.

5 Claims, 4 Drawing Sheets

COMBINATION CANCER THERAPY WITH AN AKT INHIBITOR AND OTHER ANTICANCER AGENTS

TECHNICAL FIELD

The present invention is useful in the field of cancer therapy. More precisely, combination cancer therapy with a certain Akt inhibitor and other anticancer agents such as anticancer antimetabolites, anticancer antibiotics, plant-derived anticancer agents, anticancer platinum-coordinated complex compounds, anticancer camptothecin derivatives and anticancer tyrosine kinase inhibitors of the invention is useful in the field of various cancer therapies.

BACKGROUND OF THE INVENTION

There are a large number of anticancer agents such as anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers and other anticancer agents, and one of the preferred cancer therapies has been combination chemotherapy with those anticancer agents. Their anticancer effects are, however, insufficient. One of these explanations is many types of cancers have activated PI3K pathway which prohibits tumor cells from cell death and weaken the anti-tumor efficacy by these agents. Most of these agents do not target PI3K pathway, thus did not solve the chemoresistance due to activation of this pathway. Moreover, most of these agents are not selective to tumor cells, thus side-effect was often enhanced by co-administration of cytotoxic agents. Thus, a provision of novel cancer therapy is strongly desired.

The Ser/Thr kinase Akt lies at a critical signaling node downstream of PI3K and plays an important role in promoting cell survival and inhibiting apoptosis. Direct therapeutic intervention with an Akt inhibitor may be advantageous in cancers where increased Akt signaling is associated with reduced sensitivity to cytotoxic agents or some receptor tyrosine kinase inhibitors. However, specific combination of an Akt inhibitor with other anticancer agents useful in the field of cancer therapy has not been reported.

On the other hand, WO2008/070016 and WO2008/070041 disclose 8-[4-(1-aminocyclobutyl)phenyl]-9-phenyl[1,2,4]triazolo[3,4-f]-1,6-naphthyridin-3(2H)-one or a pharmaceutically acceptable salt thereof, and various Akt inhibitors as well as other anticancer agents. However, these references do not describe the specific combination cancer therapy with the Akt inhibitor and other anticancer agents.

SUMMARY OF THE INVENTION

Figure 1:
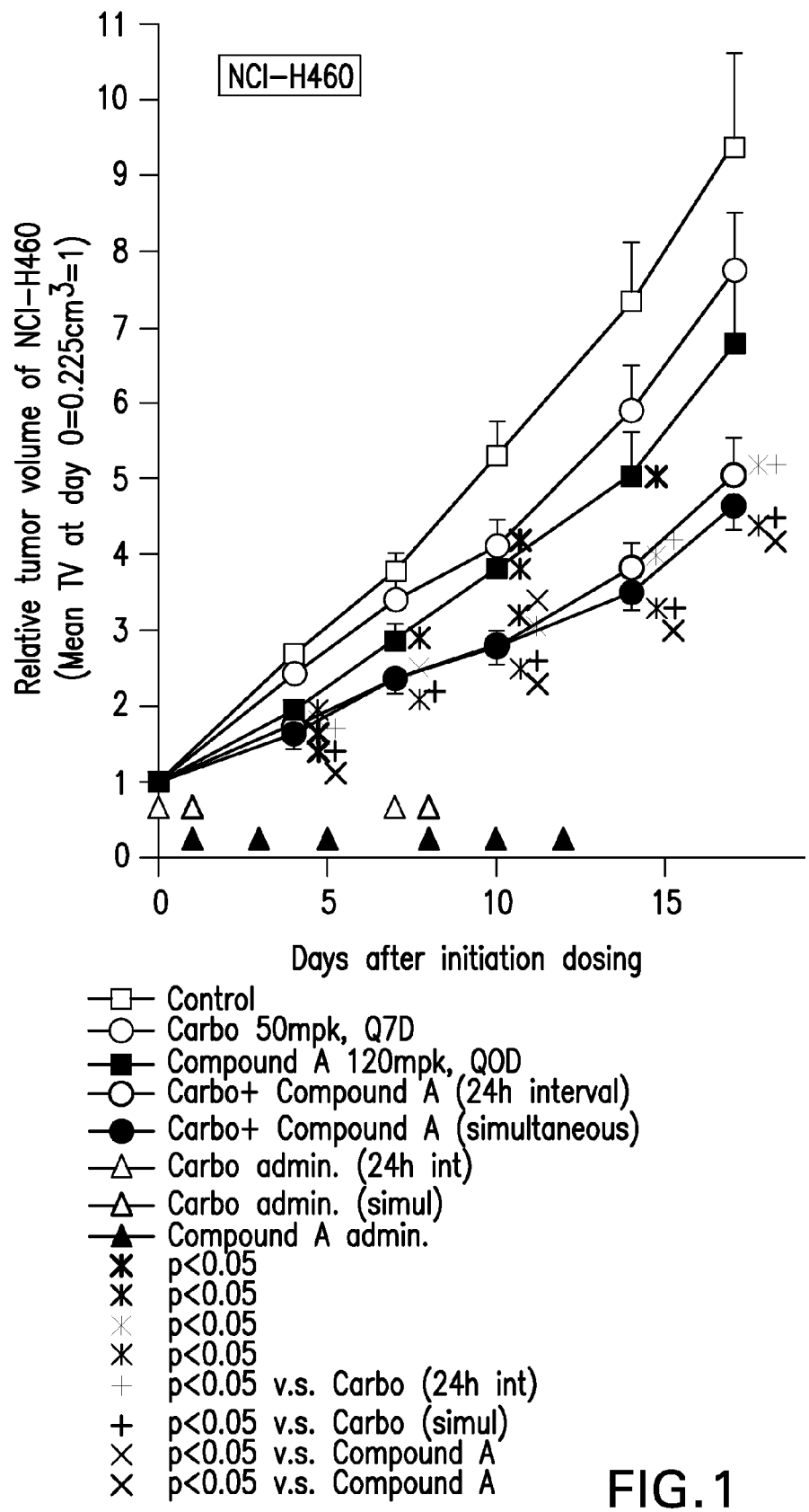
FIG. 1 is a graph that shows an enhanced effect of the combination Compound A and carboplatin on anti-tumor effect in NCI-H460 NSCLC xenograft mice.

The instant invention provides combination cancer therapy with 8-[4-(1-aminocyclobutyl)phenyl]-9-phenyl[1,2,4]triazolo[3,4-f]-1,6-naphthyridin-3(2H)-one or a pharmaceutically acceptable salt thereof as an Akt inhibitor and other anticancer agents such as anticancer antimetabolites, anticancer antibiotics, plant-derived anticancer agents, anticancer platinum-coordinated complex compounds, anticancer camptothecin derivatives and anticancer tyrosine kinase inhibitors, which exhibits an excellent anticancer activity. The invention also provides a combined anticancer agent, an anticancer agent and a pharmaceutical kit, which comprises such combination, and use of such combined anticancer agent as well as a method for the treatment of cancer.

DETAILED DESCRIPTION OF THE INVENTION

As a result of assiduous studies, the present inventors have found that a synergistically further excellent anticancer activity can be achieved by using 8-[4-(1-aminocyclobutyl)phenyl]-9-phenyl[1,2,4]triazolo[3,4-f]-1,6-naphthyridin-3(2H)-one (hereinafter, also called Compound A):

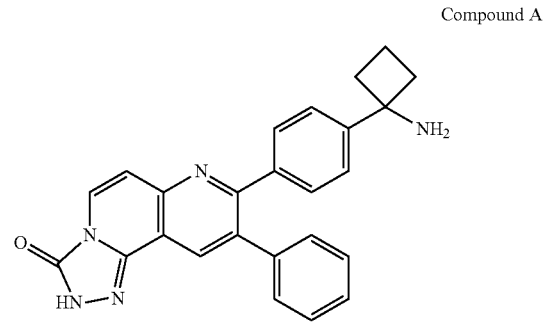 [SMILES: NC1(c2ccc(-c3nc4ccn5c(=O)[nH]nc5c4cc3-c3ccccc3)cc2)CCC1]

Compound A or a pharmaceutically acceptable salt thereof as an Akt inhibitor in combination with other anticancer agents such as anticancer antimetabolites, anticancer antibiotics, plant-derived anticancer agents, anticancer platinum-coordinated complex compounds, anticancer camptothecin derivatives and anticancer tyrosine kinase inhibitors.

The invention is thus useful in the treatment of various cancers such as brain cancer, cervicocerebral cancer, esophageal cancer, thyroid cancer, small cell lung cancer, non-small cell lung cancer, breast cancer, endometrial cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' cancer, skin cancer, malignant melanoma, neuroblastoma, osteosarcoma, Ewing's tumor, soft part sarcoma, acute leukemia, chronic lymphatic leukemia, chronic myelocytic leukemia and Hodgkin's lymphoma, in particular, breast cancer, endometrial cancer, non-small cell lung cancer, ovarian cancer and prostate cancer.

That is, the invention relates to:

(1) a combined anticancer agent for simultaneous, separate or successive administration in cancer therapy, comprising the following pharmaceutical preparations (a) and (b):
(a) a pharmaceutical preparation comprising Compound A or a pharmaceutically acceptable salt thereof, together with a pharmaceutically acceptable carrier or diluent, and
(b) a pharmaceutical preparation comprising, together with a pharmaceutically acceptable carrier or diluent, at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, or a pharmaceutically acceptable salt thereof, wherein
the anticancer antimetabolites are methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine and pemetrexed disodium;
the anticancer antibiotics are actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus and valrubicin;
the plant-derived anticancer agents are vincristine, vinblastine, vindeshine, etoposide, sobuzoxane, docetaxel, paclitaxel, and vinorelbine;
the anticancer platinum-coordinatedcomplex compounds are cisplatin, carboplatin, nedaplatin and oxaliplatin;
the anticancer camptothecin derivatives are irinotecan, topotecan and camptothecin; and
the anticancer tyrosine kinase inhibitors are gefitinib, imatinib, lapatinib and erlotinib;
(2) the combined anticancer agent according to above invention (1), wherein
the anticancer antimetabolites are 5-fluorouracil and gemcitabine;
the anticancer antibiotic is doxorubicin;
the plant-derived anticancer agents are docetaxel and paclitaxel;
the anticancer platinum-coordinatedcomplex compounds are cisplatin and carboplatin;
the anticancer camptothecin derivative is camptothecin; and
the anticancer tyrosine kinase inhibitors are lapatinib and erlotinib;
(3) the combined anticancer agent according to above invention (1), wherein the cancer is selected from breast cancer, endometrial cancer, non-small cell lung cancer, ovarian cancer and prostate cancer;
(4) an anticancer agent comprising Compound A or a pharmaceutically acceptable salt thereof, and at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as defined in above invention (1), or a pharmaceutically acceptable salt thereof, together with a pharmaceutically acceptable carrier or diluent;
(5) use of the following pharmaceutical preparations (a) and (b) for manufacturing a combined anticancer agent for simultaneous, separate or successive administration in cancer therapy:
(a) a pharmaceutical preparation comprising Compound A or a pharmaceutically acceptable salt thereof, together with a pharmaceutically acceptable carrier or diluent, and
(b) a pharmaceutical preparation comprising, together with a pharmaceutically acceptable carrier or diluent, at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as defined in above invention (1), or a pharmaceutically acceptable salt thereof;
(6) a pharmaceutical kit comprising in a first compartment Compound A or a pharmaceutically acceptable salt thereof together with a pharmaceutically acceptable carrier or diluent, and in a second compartment at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as defined in above invention (1), or a pharmaceutically acceptable salt thereof, together with a pharmaceutically acceptable carrier or diluent;
(7) a method for the treatment of cancer, which comprises administering to a subject in need thereof a therapeutically-effective amount of Compound A or a pharmaceutically acceptable salt thereof, in combination with at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as defined in above invention (1), or a pharmaceutically acceptable salt thereof; and
(8) the method according to above invention (7), wherein the cancer is selected from breast cancer, endometrial cancer, non-small cell lung cancer, ovarian cancer and prostate cancer.

The meanings of the terms used in this description are described below, and the invention is described in more detail hereinunder.

The term "simultaneous" as referred to in this description means that the pharmaceutical preparations of the combined anticancer agent of the invention are administered simultaneously in time.

The term "separate" as referred to in this description means that the pharmaceutical preparations of the combined anticancer agent of the invention are administered at different times during the course of a common treatment schedule.

The term "successive" as referred to in this description means that administration of one pharmaceutical preparation of the combined anticancer agent ((a) a pharmaceutical preparation comprising Compound A or a pharmaceutically acceptable salt thereof, together with a pharmaceutically acceptable carrier or diluent, or (b) a pharmaceutical preparation comprising, together with a pharmaceutically acceptable carrier or diluent, at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, or a pharmaceutically acceptable salt thereof, wherein the definition of each anticancer agent is the same as defined in above invention (1)) followed by administration of the other pharmaceutical preparation; after administration of one pharmaceutical preparation, the second pharmaceutical preparation can be administered substantially immediately after the first pharmaceutical preparation, or the second pharmaceutical preparation can be administered after an effective time period after the first pharmaceutical preparation; and the effective time period is the amount of time given for realization of maximum benefit from the administration of the first pharmaceutical preparation.

The term "cancer" as referred to in this description includes various sarcoma and carcinoma and includes solid cancer and hematopoietic cancer. The solid cancer as referred to herein includes, for example, brain cancer, cervicocerebral cancer, esophageal cancer, thyroid cancer, small cell lung cancer, non-small cell lung cancer, breast cancer, endometrial cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Preferably, the treatment results in cancer growth regression, or that is, it reduces the size of a detectable cancer. More preferably, the treatment results in complete disappearance of cancer.

The term "pharmaceutically acceptable salt" as referred to in this description means ordinary, pharmaceutically acceptable salt. For example, when the compound has a hydroxyl group, or an acidic group such as a carboxyl group and a tetrazolyl group, then it may form a base-addition salt at the hydroxyl group or the acidic group; or when the compound has an amino group or a basic heterocyclic group, then it may form an acid-addition salt at the amino group or the basic heterocyclic group.

The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

The term "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

With regard to each preparation or anticancer agent in the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of Compound A or other anticancer agents as an active ingredient, based on the total weight of each preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of each preparation.

Liquid preparations such as suspension or syrup for oral administration may contain, for example, 0.1 to 10% by weight of an active ingredient based on the total weight of each preparation.

Each preparation in the invention can be prepared by a person having ordinary skill in the art according to conventional methods or common techniques. For example, a preparation can be carried out, if the preparation is an oral preparation, for example, by mixing an appropriate amount of the active ingredients in the invention with an appropriate amount of lactose and filling this mixture into hard gelatin capsules which are suitable for oral administration. On the other hand, preparation can be carried out, if the preparation containing the active ingredients in the invention is an injection, for example, by mixing an appropriate amount of the active ingredients in the invention with an appropriate amount of 0.9% physiological saline and filling this mixture in vials for injection.

Compound A may be available by methods described in WO2008/070016 or WO2008/070041. Compound A may exist as tautomers and both tautomeric forms are intended to be encompassed by the scope of the compound in the invention, even though only one tautomeric structure is depicted.

For example the following is within the scope of the compound in the instant invention:

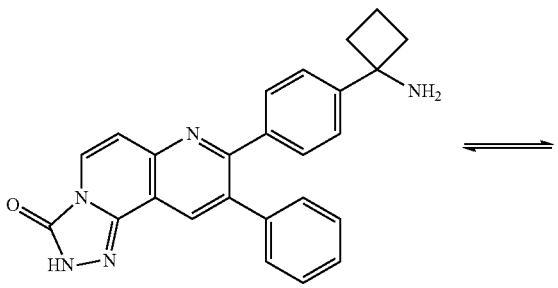 ⇌ 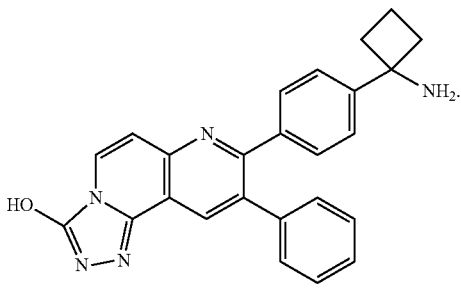

Compound A may also exist as various crystals, amorphous substances, pharmaceutically acceptable salts, hydrates and solvates of the compounds of the invention. In one embodiment, monohydrochloride of Compound A may be provided for the invention. In another embodiment, dihydrochloride of Compound A may be provided for the invention.

Further, prodrugs of Compound A may be provided for the invention. In general, such prodrugs are functional derivatives of the compounds of the invention that can be readily converted into compounds that are needed by living bodies. Accordingly, in the method of treatment of various cancers in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of the compound may include active compounds that are produced by putting the compound in a biological environment, and are within the scope of the compound in the invention.

The anticancer agent which may be combined with Compound A includes, for example, an anticancer agent selected from the group consisting of anticancer alkylating agents, anticancer antimetabolites, anticancer antibiotics, plant-derived anticancer agents, anticancer platinum coordination compounds, anticancer camptothecin derivatives, anticancer tyrosine kinase inhibitors, monoclonal antibodies, interferons, biological response modifiers, mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine and goesrelin as well as pharmaceutically acceptable salt(s) or ester(s) thereof.

The term "anticancer alkylating agent" as used in the present specification refers to an alkylating agent having anticancer activity, and the term "alkylating agent" herein generally refers to an agent giving an alkyl group in the alkylation reaction in which a hydrogen atom of an organic compound is substituted with an alkyl group. The term "anticancer alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "anticancer antimetabolite" as used in the specification refers to an antimetabolite having anticancer activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "anticancer antimetabolites" may be exemplified methotrexate, 6-mercaptopurine riboside, mercaptopurine, 5-fluorouracil (also called "5-FU"), tegafur, doxifluridine, carmofur, cytarabine, cytarabine ocfosfate, enocitabine, S-1, gemcitabine, fludarabine or pemetrexed disodium, and preferred are 5-fluorouracil, gemcitabine and the like. Gemcitabine as used in the specification refers to (+)-2'-deoxy-2',2'-difluorocytidine.

The term "anticancer antibiotic" as used in the specification refers to an antibiotic having anticancer activity, and the "antibiotic" herein includes substances that are produced by microorganisms and inhibit cell growth and other functions of microorganisms and of other living organisms. The term "anticancer antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin, and preferred are doxorubicin and the like. Doxorubicin as used in the specification refers to (2S,4S)-4-(3-amino-2,3,6-trideoxy-α-L-lyxo-hexopyranosyloxy)-2,5,12-trihydroxy-2-hydroxyacetyl-7-methoxy-1,2,3,4-tetrahydrotetracene-6,11-dione.

The term "plant-derived anticancer agent" as used in the specification includes compounds having anticancer activities which originate from plants, or compounds prepared by applying chemical modification to the foregoing compounds. The term "plant-derived anticancer agent" may be exemplified by vincristine, vinblastine, vindesine, etoposide, sobuzoxane, docetaxel, paclitaxel and vinorelbine, and preferred are docetaxel, paclitaxel and the like, in particular, docetaxel. Docetaxel as used in the specification refers to (−)-(1S,2S,3R,4S,5R,7S,8S,10R,13S)-4-acetoxy-2-benzoyloxy-5,20-epoxy-1,7,10-trihydroxy-9-oxotax-11-ene-13-yl (2R,3S)-3-tert-butoxycarbonylamino-2-hydroxy-3-phenylpropionate. Paclitaxel as used in the specification refers to (−)-(1S,2S,3R,4S,5R,7S,8S,10R,13S)-4,10-diacetoxy-2-benzoyloxy-5,20-epoxy-1,7-dihydroxy-9-oxotax-11-en-13-yl (2R,3S)-3-benzoylamino-2-hydroxy-3-phenylpropionate.

The term "anticancer camptothecin derivative" as used in the specification refers to compounds that are structurally related to camptothecin and inhibit cancer cell growth, including camptothecin per se. The term "anticancer camptothecin derivative" is not particularly limited to, but may be exemplified by, camptothecin, 10-hydroxycamptothecin, topotecan, irinotecan or 9-aminocamptothecin, with camptothecin being preferred. Further, irinotecan is metabolized in vivo and exhibits anticancer effect as SN-38. The action mechanism and the activity of the camptothecin derivatives are believed to be virtually the same as those of camptothecin (e.g., Nitta, et al., *Gan to Kagaku Ryoho,* 14, 850-857 (1987)). Camptothecin as used in the specification refers to 4-ethyl-4-hydroxy-1H-pyrano[3',4':6,7]indolizino[1,2-b]quinoline-3,14-(4H,12H)-dione.

The term "anticancer platinum coordination compound" as used in the specification refers to a platinum coordination compound having anticancer activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred are carboplatin, cisplatin and the like, in particular, carboplatin. Further, other anticancer platinum coordination compounds mentioned in the specification are known and are commercially available and/or producible by a person having ordinary skill in the art by conventional techniques. Cisplatin as used in the specification refers to cis-diaminedichloroplatinum(II). Carboplatin as used in the specification refers to cis-diammine(1,1-cyclobutanedicarboxylato)platinum(II).

The term "anticancer tyrosine kinase inhibitor" as used in the specification refers to a tyrosine kinase inhibitor having anticancer activity, and the term "tyrosine kinase inhibitor" herein refers to a chemical substance inhibiting "tyrosine kinase" which transfers a $\gamma$-phosphate group of ATP to a hydroxyl group of a specific tyrosine in protein. The term "anticancer tyrosine kinase inhibitor" may be exemplified by gefitinib, imatinib, lapatinib or erlotinib, and preferred are lapatinib, erlotinib and the like. In particular, EGFR/HER2 inhibitor such as lapatinib and EGFR inhibitor such as erlotinib are preferred. Lapatinib as used in the specification refers to N-[3-Chloro-4-[(3-fluorobenzyl)oxy]phenyl]-6-[5-[[[2-(methylsulfonyl)ethyl]amino]methyl]-2-furyl]-4-quinazolinamine. Erlotinib as used in the specification refers to N-(3-ethynylphenyl)-6,7-bis(2-methoxyethoxy)-4-quinazolinamine.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having anticancer activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon $\alpha$, interferon $\alpha$-2a, interferon $\alpha$-2b, interferon $\beta$, interferon $\gamma$-1a and interferon $\gamma$-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The above-described terms "anticancer alkylating agent", "anticancer antimetabolite", "anticancer antibiotic", "plant-derived anticancer agent", "anticancer platinum coordination compound", "anticancer camptothecin derivative", "anticancer tyrosine kinase inhibitor", "monoclonal antibody", "interferon", "biological response modifier", mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine and goesrelin are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; the process for preparation of lapatinib is described, for example, in U.S. Pat. No. 6,713,485; and the process for preparation of rituximab is described, for example, in JP-W No. 2-503143.

The above-mentioned anticancer alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned anticancer antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned anticancer antibiotics are commercially available, as exemplified by the following: actinomycin D from Banyu Pharmaceutical Co., Ltd. as Cosmegen (tradename); doxorubicin from Kyowa Hakko Kogyo Co., Ltd. as Adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived anticancer agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned anticancer platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned anticancer camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned anticancer tyrosine kinase inhibitors are commercially available, as exemplified by the following: gefitinib from AstriZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Imunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as Krestin (tradename); lentinan from Aventis Corp. as Lentinan (tradename); sizofuran from Kaken Seiyaku Co., Ltd. as Sonifiran (tradename); picibanil from Chugai Pharmaceutical Co., Ltd. as Picibanil (tradename); and ubenimex from Nippon Kayaku Co., Ltd. as Bestatin (tradename).

The above-mentioned other miscellaneous anticancer agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goesrelin from AstraZeneca Corp. as Zoladex (tradename).

In one embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising 5-fluorouracil or a pharmaceutically acceptable salt thereof, together with a pharmaceutically acceptable carrier or diluent.

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising gemcitabine or a pharmaceutically acceptable salt thereof, together with a pharmaceutically acceptable carrier or diluent.

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising doxorubicin or a pharmaceutically acceptable salt thereof, together with a pharmaceutically acceptable carrier or diluent.

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising docetaxel or a pharmaceutically acceptable salt thereof, together with a pharmaceutically acceptable carrier or diluent.

In yet another embodiment, the combined anticancer agent for separate or successive administration of the invention comprises the following pharmaceutical preparations (a) and (b):
(a) a pharmaceutical preparation comprising Compound A or a pharmaceutically acceptable salt thereof, together with a pharmaceutically acceptable carrier or diluent, and
(b) a pharmaceutical preparation comprising docetaxel or a pharmaceutically acceptable salt thereof, together with a pharmaceutically acceptable carrier or diluent, wherein the preparation
(a) is administered after the administration of preparation (b).

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising paclitaxel or a pharmaceutically acceptable salt thereof, together with a pharmaceutically acceptable carrier or diluent.

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising cisplatin or a pharmaceutically acceptable salt thereof, together with a pharmaceutically acceptable carrier or diluent.

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising carboplatin or a pharmaceutically acceptable salt thereof, together with a pharmaceutically acceptable carrier or diluent.

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising camptothecin or a pharmaceutically acceptable salt thereof, together with a pharmaceutically acceptable carrier or diluent.

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising lapatinib or a pharmaceutically acceptable salt thereof, together with a pharmaceutically acceptable carrier or diluent.

In another embodiment, the combined anticancer agent of the invention comprises pharmaceutical preparations (a) a pharmaceutical preparation comprising Compound A or a pharmaceutically acceptable salt thereof, together with a pharmaceutically acceptable carrier or diluent, and (b) a pharmaceutical preparation comprising erlotinib or a pharmaceutically acceptable salt thereof, together with a pharmaceutically acceptable carrier or diluent.

Compound A in the invention can be used in combination with other anticancer agent and optionally with radiation therapy. The individual ingredients for such combination may be administered at different times or at the same time as divided preparations or one preparation during the term of treatment. Accordingly, the invention should be so interpreted that it includes all modes of administration at the same time or at different times, and the administration in this invention should be interpreted so. The scope of the combination of the invention should include, in principle, any and every combination thereof with any and every pharmaceutical agent useful for the treatment of cancer.

Radiation therapy itself means an ordinary method in the field of treatment of cancer. For radiation therapy, employable are various radiations such as X-ray, γ-ray, neutron ray, electron beam, proton beam; and radiation sources. In a most popular radiation therapy, a linear accelerator is used for irradiation with external radiations, γ-ray.

The combined anticancer agent comprising Compound A and at least one other anticancer agent may be readily produced by anyone skilled in the art according to ordinary methods or conventional techniques.

The above-mentioned combination includes not only the anticancer agent that contains one other active substance but also those containing two or more other active substances.

The invention also relates to a pharmaceutical kit comprising in a first compartment Compound A or a pharmaceutically acceptable salt thereof together with a pharmaceutically acceptable carrier or diluent, and in a second compartment at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as defined in above invention (1), or a pharmaceutically acceptable salt thereof, together with a pharmaceutically acceptable carrier or diluent.

The pharmaceutical kit provides for the combined anticancer agent of the invention.

The invention also relates to a pharmaceutical kit comprising in a first compartment Compound A or a pharmaceutically acceptable salt thereof together with a pharmaceutically acceptable carrier or diluent, and in a second compartment at least one anticancer agent selected from the group consisting of 5-fluorouracil, gemcitabine, doxorubicin, docetaxel, paclitaxel, cisplatin, carboplatin, camptothecin, lapatinib and erlotinib, or a pharmaceutically acceptable salt thereof, together with a pharmaceutically acceptable carrier or diluent.

In one embodiment of the kit of the invention the anticancer agent in the second compartment is 5-fluorouracil.

In another embodiment of the kit of the invention the anticancer agent in the second compartment is gemcitabine.

In another embodiment of the kit of the invention the anticancer agent in the second compartment is doxorubicin.

In another embodiment of the kit of the invention the anticancer agent in the second compartment is docetaxel.

In another embodiment of the kit of the invention the anticancer agent in the second compartment is paclitaxel.

In another embodiment of the kit of the invention the anticancer agent in the second compartment is cisplatin.

In another embodiment of the kit of the invention the anticancer agent in the second compartment is carboplatin.

In another embodiment of the kit of the invention the anticancer agent in the second compartment is camptothecin.

In another embodiment of the kit of the invention the anticancer agent in the second compartment is lapatinib.

In another embodiment of the kit of the invention the anticancer agent in the second compartment is erlotinib.

The invention also relates to a method for the treatment of cancer, which comprises administering to a subject in need thereof a therapeutically-effective amount of Compound A or a pharmaceutically acceptable salt thereof, in combination with at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as described above, or a pharmaceutically acceptable salt thereof.

In the method according to the invention, preferred therapeutic unit may vary in accordance with, for example, the administration route of Compound A, the type of Compound A used, and the dosage form of Compound A used; the type, administration route and dosage form of the other anticancer agent used in combination; and the type of cells to be treated, the condition of patient, and the like. The optimal treatment under the given conditions can be determined by a person skilled in the art, based on the set conventional therapeutic unit and/or based on the content of the present specification.

In the method according to the invention, the therapeutic unit for Compound A may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other anticancer agent used in combination with Compound A is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m$^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m² is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m² is administered once a day by intravenous drip infusion for 3 or 4 times at an interval of one week, followed by withdrawal from medication for at least two weeks.

The therapeutic unit for topotecan is such that, for example, 1.5 mg/m² is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m² is administered on the first day by intravenous drip infusion, and then 250 mg/m² is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m² of 5-FU and 200 mg/m² of leucovorin are administered from the first day to the fifth day by intravenous drip infusion, and this course is repeated at an interval of 4 weeks.

The invention is described more concretely with reference to the following pharmacological Test Examples, which, however, are not intended to restrict the scope of the invention. Monohydrochloride or dihydrochloride of Compound A was used in the following Examples.

EXAMPLES

Methods of Pharmaceutical Combinations of Akt Inhibitor with Cancer Treatment Agents Example 1

TABLE 1

Synergistic effect of the combination Compound A and carboplatin on in vitro proliferation/viability of ovarian, prostate, and NSCLC cell lines

| | | Fractional inhibition of proliferation caused by combination of carboplatin and Compound A | | |
|---|---|---|---|---|
| | | $ED_{50}$ | $ED_{75}$ | $ED_{90}$ |
| Cell line name | Cancer types | Combination index for above fractional inhibition | | |
| A2780 | Ovarian | 0.5 | 0.4 | 0.4 |
| OVCAR3 | Ovarian | 1.0 | 0.5 | 0.6 |
| LNCaP | Prostate | 0.7 | 0.6 | 0.6 |
| H460 | NSCLC | 0.4 | 0.3 | 0.4 |
| H1993 | NSCLC | 0.8 | 0.4 | 0.5 |
| H661 | NSCLC | 0.5 | 0.4 | 0.4 |
| H441 | NSCLC | 0.5 | 0.6 | 0.8 |
| H522 | NSCLC | 0.9 | 0.7 | 0.5 |

The relationship between carboplatin and Compound A concentrations and inhibition of proliferation/viability of each tumor cell line was measured with cells simultaneously treated with both agents for 72 h. The data were analyzed bu using CalcuSyn software that calculates the combination index (CI) for each combination of carboplatin and Compound A. CI < 0.9 indicates synergism; CI = 0.9 to 1.1 indicates additivity; and CI > 1.1 indicates antagonism.

Materials & Methods

T1.1. Compounds

Compound A was dissolved in dimethyl sulphoxide (DMSO) (SIGMA, #D2650) to make 10 mM stock solution and stored at −20° C. Carboplatin (SIGMA, #C2538) was dissolved in sterile distilled water and stored at −20° C.

T1.2. Cell Lines

Human ovarian cancer cell (A2780) was obtained from the European Collection of Cell Culture (ECACC). Human ovarian cancer cells (OVCAR3), human prostate cancer cells (LNCaP), human non-small cell lung cancer (NSCLC) cells (NCI-H460, NCI-H1993, NCI-H661, NCI-H441, and NCI-H1522) were obtained from the American Type Culture Collection (ATCC). All cell lines were cultured in RPMI-1640 containing heat-inactivated 10% fetal bovine serum (FBS) in a humidified incubator at 37° C. in 5% $CO_2$, T1.3. In Vitro Combination of Compound A with Carboplatin All cell lines (total 8 cell lines) were seeded at 2,000 cells/well in RPMI 1640 supplemented with 10% heat-inactivated FBS in 96 well tissue culture plates (CORNING #3340) and incubated at 37° C. in 5% $CO_2$ overnight. Then Compound A or carboplatin was added as a dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminescence signal was read using a ARVO-SX multimode plate reader (Perkin-Elmer). Percent inhibition of cell growth was calculated relative to the vehicle treated control. Concentration of the compound that inhibit 50% of control cell growth (IC50) was interpolated using nonlinear regression and the equation;

$$Y=\text{Bottom}+(\text{Top}-\text{Bottom})/(1+10\hat{\,}((\text{Log}\,ED50-X)*\text{Hill slope}))$$

X is the logarithm of concentration, Y is the response. Y starts at Bottom and goes to Top with a sigmoid shape.

A 2- or 3-fold serial dilution series of concentrated Compound A/carboplatin combinations was prepared, in which the concentration ratio of the two drugs was fixed and equal to 1050 ratio of Compound A and carboplatin determined in single agent titrations described above. Corresponding single agent dilution series of concentrated Compound A and carboplatin were also prepared. The three dilution series were then tested in the proliferation/viability assay as described above. The data were analyzed using CalcuSyn software (BIOSOFT) that calculates combination index (CI) for each combination of Compound A/carboplatin as described below. Combination index values were generated by inserting the interpolated values into the mutually exclusive equation derived by Chou and Talalay.

T1.4. Combination Index

Synergistic interaction between compounds was analyzed by the median effect method described by Chou and Talalay (Adv. Enzyme Regul. 22: 27-55, 1984). Studies were first conducted to determine the potency of Compound A or combination partner (Drug-A) as single agent in inhibiting proliferation/viability of tumor cells. The $IC_{50}$ values of each single agent were determined by fitting data to four parameter dose-response equation. Percent inhibition of cell growth was calculated relative to vehicle treated control wells. Concentration of compound that inhibit 50% of control cell growth (1050) was interpolated using nonlinear regression with the following equation;

$$Y=\text{Bottom}+(\text{Top}-\text{Bottom})/(1+10\hat{\,}((\text{Log}\,ED50-X)*\text{Hill slope}))$$

X is the logarithm of concentration, Y is the response. Y starts at Bottom and goes to Top with a sigmoid shape.

The fixed ratio experimental design was then used to compare of various Compound A/Drug-A combinations and corresponding single agent treatments.

The combination index was calculated by the following equation based on doses that had equivalent effects in tumor cell proliferation/viability assay;

$$CI=(D1/D1_c)+(D2/D2_c)$$

where D1 and D2 represent doses for each drug alone that effect x % of cells and $D1_c$ and $D2_c$ are the concentrations of combined drugs that effect the same percentage of cells. D1 and D2 are known from the composition of the combination and $D1_c$ and $D2_c$ can be calculated from the equation;

$$D_c=D_m*[f_a/(1-f_a)]^{1/m}$$

where $D_m$ is the concentration of drugs giving 50% effect, $f_a$ is the fraction affected, and m is the slope from the median effect plot of log $(f_a/f_u)$ where $f_u$ is the fraction unaffected versus log (D). A CI equal to 1 signifies an additive effect, less than 1 a synergistic effect, and greater than 1 an antagonistic effect.

Example 2

Enhanced Effect of the Combination Compound A and Carboplatin on Anti-Tumor Effect in NCI-H460 NSCLC Xenograft Mice (FIG. 1)

Materials & Methods

Human non-small cell lung cancer cell (NCI-H460) was obtained from the American. Type Culture. Collection (ATCC). NCI-H460 cells were cultured in RPMI-1640 containing heat-inactivated 10% fetal bovine serum (FBS) in a humidified incubator at 37° C. in 5% $CO_2$. These cells were suspended in 50% Matrigel (BD Biosciences) diluted with PBS, and were subcutaneously transplanted into side flank of CD1-nude mice by using needle and syringe ($1.3\times10^7$ NCI-H460 cells/100 μL,) under isoflurane anesthesia. Mice were randomized according to NCI-H460 tumor volumes and distributed into treatment groups of 5 mice with approximately equivalent ranges of tumor volumes between treatment groups.

On 11th day post-tumor transplantation, vehicle (saline) or carboplatin (50 mg/kg, dissolved with saline, Bristol-Myers Squibb (Paraplatin)) was administered intravenously (day 1), and on day 1, 3, 5, 8, 10, 12 vehicle (30% captisol) or Compound A (120 mg/kg, dissolved with 30% captisol) was administered orally for 2 weeks. Measurement of tumor volume, body weight and gross observation were performed.

Tumor volume was measured as follows; tumor diameters were measured with digital caliper at the day 0, 4, 7, 10, 14, and 17 and tumor volume ($mm^3$) was calculated by the following formula:

$$\text{Tumor volume (mm3)}=\text{length}\times(\text{width})^2\times0.5$$

Relative tumor volume=$V/V_0$

Where $V_0$ equals the tumor volume at day 0 and V equals the tumor volume on different observation days (day 4, 7, 10, 14 or 17).

$$\%\ T/C=100\times\Delta T/\Delta C\ if\ \Delta T>0,$$

or $$\%\ T/C=100\times\Delta T/Ti\ if\ \Delta T<0$$

Where:

ΔT equals the change in mean relative tumor volume to initial relative tumor volume for the treatment group ΔC equals the change in mean relative tumor volume to initial relative tumor volume for the vehicle control group, and Ti equals to the initial relative tumor volumes for the treatment group Low positive values of % T/C reflect control of tumor growth, while negative values indicate tumor regression. According to National Cancer Institute (NCI) guidelines, a % T/C≦42% is considered demonstration of significant anti-tumor activity; while a % T/C<10% is indicative of a highly active agent.

Statistical analysis was performed using repeated measure ANOVA followed by Dunnett.

Example 3

TABLE 2

Synergistic effect of the combination Compound A and gemcitabine on in vitro proliferation/viability of ovarian and NSCLC cell lines

| Cell line name | Cancer types | Fractional inhibition of proliferation caused by combination of gemcitabine and Compound A | | |
|---|---|---|---|---|
| | | $ED_{50}$ | $ED_{75}$ | $ED_{90}$ |
| | | Combination index for above fractional inhibition | | |
| A2780 | Ovarian | 0.6 | 0.4 | 0.4 |
| H647 | NSCLC | 0.2 | 0.1 | 0.1 |
| H441 | NSCLC | 0.5 | 0.4 | 0.4 |
| H1703 | NSCLC | 0.4 | 0.4 | 0.7 |
| H661 | NSCLC | 0.8 | 0.6 | 0.5 |
| H460 | NSCLC | 0.3 | 0.4 | 0.6 |
| H1915 | NSCLC | 0.5 | 0.4 | 0.3 |
| H1975 | NSCLC | 0.5 | 0.3 | 0.2 |
| H2122 | NSCLC | 0.8 | 0.5 | 0.3 |
| H2087 | NSCLC | 1.0 | 0.7 | 0.6 |
| H520 | NSCLC | 0.5 | 0.4 | 0.4 |

The relationship between gemcitabine and Compound A concentrations and inhibition of proliferation/viability of each tumor cell line was measured for cells treated simultaneously with both agents for 72 h. The data were analyzed by using CalcuSyn software that calculates the combination index (CI) for each combination of gemcitabine and Compound A. CI < 0.9 indicates synergism; CI = 0.9 to 1.1 indicates additivity; and CI > 1.1 indicates antagonism.

Materials & Methods

T2.1. Compounds

Compound A was dissolved in dimethyl sulphoxide (DMSO) (SIGMA, #D2650) to make 10 mM stock solution and stored at −20° C. Gemcitabine was prepared by dissolving Gemzar® Injection (Eli Lilly Japan K.K.) with phosphate buffered saline (PBS), pH 7.4 (Invitrogen, #10010-049) and stored at −20° C.

T2.2. Cell Lines

Human ovarian cancer cell (A2780) was obtained from the European Collection of Cell Culture (ECACC). Human non-small cell lung cancer cells (NCI-H647, NCI-11441, NCI-H1703, NCI-H661, NCI-H460, NCI-H1915, NCI-H1975, NCI-H2122, NCI-H2087 and NCI-H520) were obtained from the American Type Culture Collection (ATCC). All cell lines were cultured in RPMI-1640 containing heat-inactivated 10% fetal bovine serum (FBS) in a humidified incubator at 37° C. in 5% $CO_2$.

T23. In Vitro Combination of Compound A with Gemcitabine

All cell lines (total 11 cell lines) were seeded at 2,000 cells/well in RPMI 1640 supplemented with 10% heat-inactivated FBS in 96 well tissue culture plates (CORNING #3340) and incubated at 37° C. in 5% $CO_2$ overnight. Then Compound A, gemcitabine or the combination of the two agents was added as a 2-fold dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminescence signal was read using a ARVO-SX multi-mode plate reader (Perkin-Elmer). Combination index was determined by the same method as described in section T1.3.

Example 4

Figure 2:
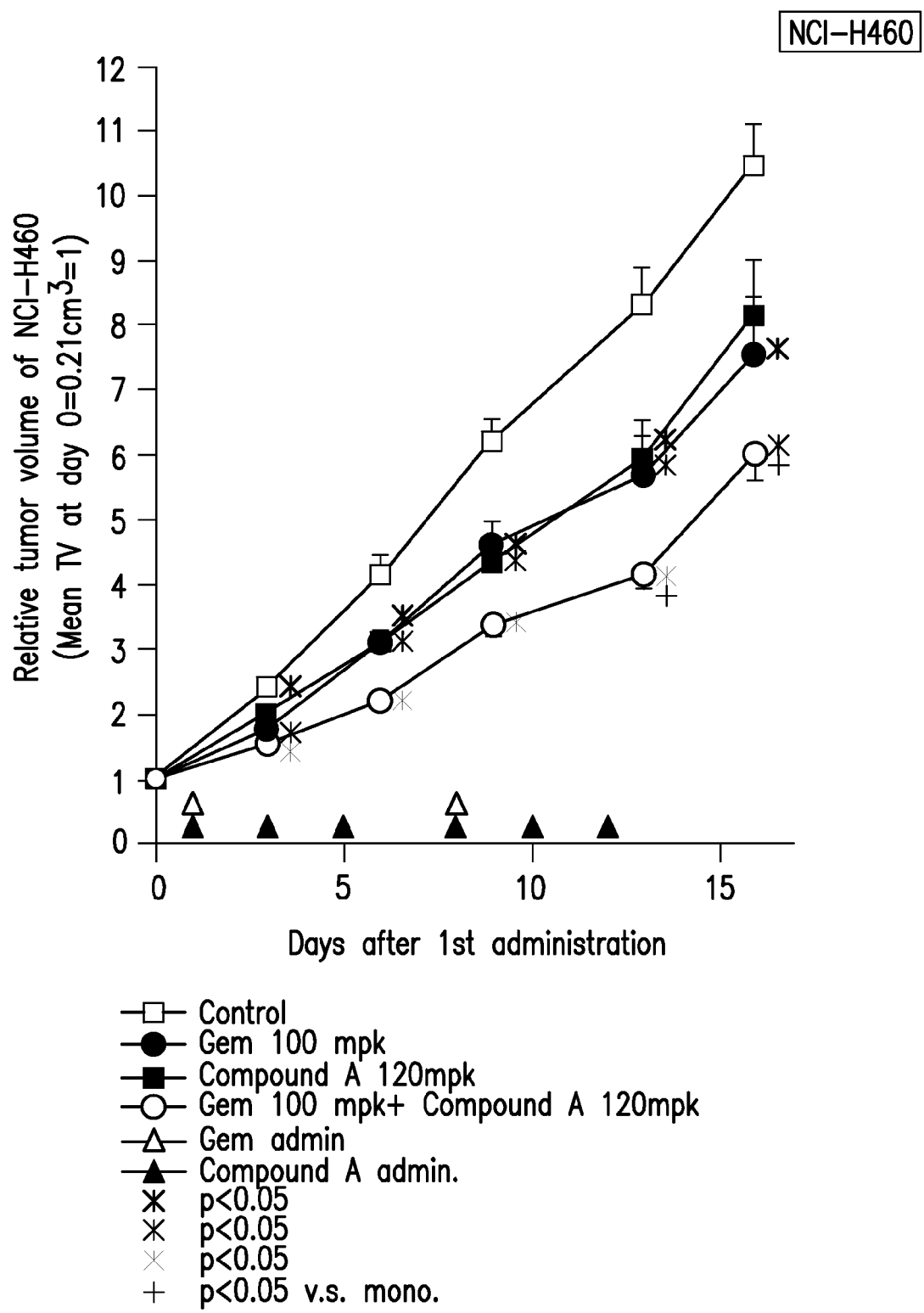
FIG. 2 is a graph that shows an enhanced effect of the combination Compound A and gemcitabine on anti-tumor effect in NCI-H460 NSCLC xenograft mice.

Enhanced Effect of the Combination Compound A and Gemcitabine on Anti-Tumor Effect in NCI-H460 NSCLC Xenograft Mice (FIG. 2)

Materials & Methods

Human non-small cell lung cancer cells (NCI-H460) was obtained from the American Type Culture Collection (ATCC). NCI-H460 cells were cultured in RPMI-1640 containing heat-inactivated 10% fetal bovine serum (FBS) in a humidified incubator at 37° C. in 5% $CO_2$. These cells were suspended in 50% Matrigel (BD Biosciences) diluted with PBS, and were subcutaneously transplanted into side flank of CD1-nude mice by using needle and syringe (1.3×10$^7$ NCI-H460 cells/100 μL,) under isoflurane anesthesia. Mice were randomized according to NCI-H460 tumor volumes and distributed into treatment groups of 5 mice with approximately equivalent ranges of tumor volumes between treatment groups.

On 7th day post-tumor transplantation, vehicle (saline) or gemcitabine (100 mg/kg, dissolved with saline, Eli Lilly (Gemzar)) was administered intravenously (day 0) once a week for two weeks. Vehicle (30% captisol) or Compound A (120 mg/kg, dissolved with 30% captisol) was administered orally three times per week for 2 weeks. For binary combination, Compound A was administered on the same day as gemcitabine. Tumor volume was measured with digital caliper at the day 0, 3, 6, 9, 13 and 16. Measurement of body weight and gross observation were performed. Anti-tumor efficacy was monitored by the same method as described in section FIG. 1.

Example 5

TABLE 3

Synergistic effect of the combination Compound A and docetaxel on in vitro proliferation/viability of breast cancer cell line

| Breast cancer cell line name | Fractional inhibition of proliferation caused by combination of docetaxel and Compound A | | |
|---|---|---|---|
| | $ED_{50}$ | $ED_{75}$ | $ED_{90}$ |
| | Combination index for above fractional inhibition | | |
| ZR-75-1 | 0.1 | 0.2 | 0.4 |
| MDA-MB-453 | 1.2 | 0.6 | 0.3 |
| BT-20 | 1 | 0.7 | 0.5 |
| BT-474 | 0.6 | 0.8 | 1.1 |
| MCF-7 | 0.7 | 0.5 | 0.3 |
| HCC70 | 0.9 | 0.7 | 0.5 |
| MDA-MB-231 | 0.9 | 0.7 | 0.7 |
| MDA-MB-468 | 0.9 | 0.8 | 0.9 |
| SK-BR-3 | 0.8 | 0.7 | 0.8 |

The relationship between docetaxel and Compound A concentration and inhibition of proliferation/viability of each tumor cell line was measured with cells treated by one of the following three ways: 1) 24 hours with docetaxel alone followed by vehicle for 72 hours; 2) 24 hours with docetaxel followed by Compound A for 72 hrs; 3) 24 hours with vehicle followed by Compound A alone for 72 hours. The data were analyzed using CalcuSyn software that calculates combination index (CI) for each combination of docetaxel/Compound A. CI < 0.9 indicates synergism; CI = 0.9 to 1.1 indicates additivity and CI > 1.1 indicates antagonism.

Materials & Methods

T3.1. Compounds

Compound A was dissolved in dimethyl sulphoxide (DMSO) (SIGMA, #D2650) to make 10 mM stock solution and stored at −20° C. Docetaxel (SIGMA, #01885) was dissolved in DMSO and stored at −20° C.

T3.2. Cell Lines

Human breast cancer cell lines (ZR-75-1, MDA-MB-453, BT-20, BT-474, MCF-7, HCC70, MDA-MB-231, MDA-MB-468, and SK-Br-3) were obtained from the American Type Culture Collection (ATCC). All cell lines were cultured in RPMI-1640 containing heat-inactivated 10% fetal bovine serum (FBS) in a humidified incubator at 37° C. in 5% $CO_2$.

T3.3. In Vitro Combination of Compound A with Docetaxel

All breast cancer cell lines (total 9 cell lines) were seeded at 3,000 cells/well in RPMI 1640 supplemented with 10% heat-inactivated FBS in 96 well tissue culture plates (CORNING #3340) and incubated at 37° C. in 5% $CO_2$. Approximately 24 hours after plating, cells were sequentially exposed to two-fold serial dilutions of docetaxel and Compound A in medium containing 1% DMSO with following regimens: 1) 24 hours with docetaxel alone followed by vehicle (final 0.1%

DMSO) for 72 hours; 2) 24 hours with docetaxel followed by washout and then Compound A for 72 hours; 3) 24 hours with vehicle (final 0.1% DMSO) followed by Compound A alone for 72 hours. The final DMSO concentration in each assay was 0.1%. After the plates were incubated at 37° C. in 5% $CO_2$, the number of viable cells was measured using ATPlite Luminescence Assay System (Perkin-Elmer #6016949). The luminescence signal was read using a Victor3 multimode plate reader (Perkin-Elmer). Combination index was determined by the same method as described in section T1.3.

Example 6

Figure 3:
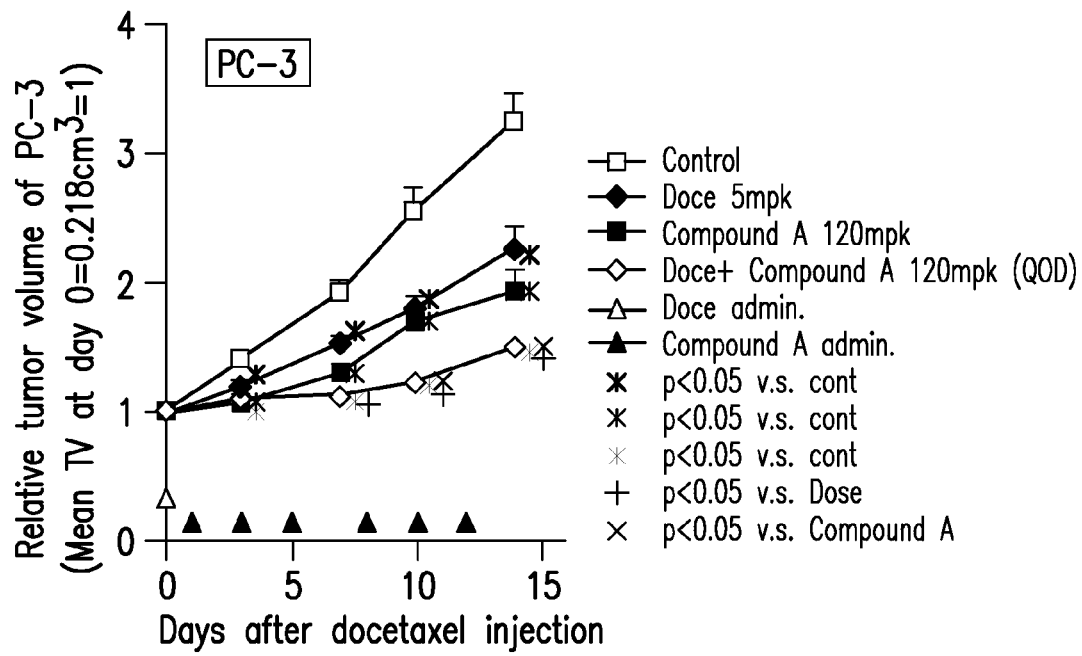
FIG. 3 is a graph that shows an enhanced effect of the combination Compound A and docetaxel on anti-tumor effect in PC-3 prostate xenograft mice.

Enhanced Effect of the Combination Compound A and Docetaxel on Anti-Tumor Effect in PC-3 Prostate Xenograft Mice (FIG. 3)

Materials & Methods

PC-3 cells are human prostate cancer cells originally obtained from the American Type Culture Collection (ATCC). PC-3 cells were cultured in RPMI-1640 containing heat-inactivated 10% fetal bovine serum (FBS) in a humidified incubator at 37° C. in 5% $CO_2$. These cells were suspended in 50% Matrigel (BD Biosciences) diluted with PBS, and were subcutaneously transplanted into side flank of CD1-nude mice by using needle and syringe ($2 \times 10^7$ PC-3 cells/200 μL,) under isoflurane anesthesia. Mice were randomized according to PC-3 tumor volumes and distributed into treatment groups of 5 mice with approximately equivalent ranges of tumor volumes between treatment groups.

On 25th day post-tumor transplantation, vehicle (Saline with 0.73% EtOH) or Docetaxel (5 mg/kg, Sanofi aventis) was administered intravenously (day 0), and on day 1, 3, 5, 8, 10, 12 vehicle (30% captisol) or Compound A (80, 120 mg/kg) was administered orally for 2 weeks. Measurement of tumor volume, body weight and gross observation were performed. Anti-tumor efficacy was monitored by the same method as described in section FIG. 1.

Example 7

TABLE 4

Synergistic effect of the combination Compound A and other standard of care agents (SOCs) on in vitro proliferation/viability of A2780 ovarian cancer cell line

| Combination partner | Mode of action | Fractional inhibition of proliferation caused by combination of carboplatin and Compound A | | | Caspase-3/7 fold induction at 24 h | | |
|---|---|---|---|---|---|---|---|
| | | $ED_{50}$ | $ED_{75}$ | $ED_{90}$ | (fold of DMSO control) | | |
| | | Combination index for above | | | Compound A (nM) | | |
| SOCs | action | fractional inhibition | | | 62.5 | 250 | 1000 |
| Doxorubicin | Topoisomerase inhibitor | 0.70 | 0.43 | 0.27 | 1.6 | 2.8 | 4.1 |
| Camptothecin | Topoisomerase inhibitor | 0.56 | 0.40 | 0.29 | 1.9 | 2.6 | 4.0 |
| 5-FU | Antimetabolites | 0.68 | 0.54 | 0.53 | 1.5 | 1.7 | 2.5 |

The relationship between SOC and Compound A concentrations and inhibition of proliferation/viability in A2780 cells was measured after simultaneous treatment with both agents for 72 h. The data were analyzed by using CalcuSyn software that calculates the combination index (CI) for each combination of SOCs and Compound A. CI < 0.9 indicates synergism; CI = 0.9 to 1.1 indicates additivity; and CI > 1.1 indicates antagonism. Caspase-3/7 induction was determined by a luminescent assay with luminogenic caspase-3/7 substrate (Caspase-Glo 3/7 assay; Promega).

Materials & Methods

T4.1. Compounds

Compound A was dissolved in dimethyl sulphoxide (DMSO) (SIGMA, #D2650) to make 10 mM stock solution and stored at −20° C. Doxorubicin (SIGMA, #D1515) was dissolved in sterile distilled water and stored at −20° C. Camptothecin (SIGMA, #C9911) was dissolved in DMSO and stored at −20° C. 5-Fluorouracil (5-FU) (SIGMA, #F6627) was dissolved in PBS and stored at −20° C.

T4.2. Cell Lines

Human ovarian cancer cell (A2780) was obtained from the European Collection of Cell Culture (ECACC). A2780 cells were cultured in RPMI-1640 containing heat-inactivated 10% fetal bovine serum (FBS) in a humidified incubator at 37° C. in 5% $CO_2$.

T4.3. In Vitro Combination of Compound A with Doxorubicin

The cells were seeded at 2,000 cells/well in RPMI 1640 supplemented with 10% heat-inactivated FBS in 96 well tissue culture plates (CORNING #3340) and incubated at 37° C. in 5% $CO_2$ overnight. On the next day Compound A, doxorubicin or the combination of the two agents was added as a 2-fold dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminescence signal was read using a ARVO-SX multimode plate reader (Perkin-Elmer). Combination index was determined by the same method as described in section T1.3.

T4.4. In Vitro Combination of Compound A with Camptothecin

The cells were seeded at 2,000 cells/well in RPMI 1640 supplemented with 10% heat-inactivated FBS in 96 well tissue culture plates (CORNING #3340) and incubated at 37° C. in 5% $CO_2$ overnight. On the next day Compound A, camptothecin or the combination of the two agents was added as a 2-fold dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminescence signal was read using a ARVO-SX multimode plate reader (Perkin-Elmer). Combination index was determined by the same method as described in section T1.3.

T4.5. In Vitro Combination of Compound A with 5-FU

The cells were seeded at 2,000 cells/well in RPMI 1640 supplemented with 10% heat-inactivated FBS in 96 well tissue culture plates (CORNING #3340) and incubated at 37° C. in 5% $CO_2$ overnight. On the next day Compound A, 5-FU or the combination of the two agents was added as a 2-fold dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminescence signal was read using a ARVO-SX multimode plate reader (Perkin-Elmer). Combination index was determined by the same method as described in section T1.3.

T4.6. Caspase-3/7 Assay

A2780 ovarian cancer cell line was cultured at 37° C. in complete medium (RPMI-1640 supplemented with 10% heat-inactivated FBS) and plated at 2,000 cells/well in 96 well assay plates (CORNING #3340). Studies were first conducted to determine the potency of Compound A or combination partner as single agent in inhibiting proliferation/viability of tumor cells. Cytotoxic agents (camptothecin, doxorubicin and 5-FU) were diluted to 100 uM with culture medium, and then serially diluted by 3-fold with culture medium for doxorubicin and 5-FU, or with 1% DMSO/culture medium for camptothecin. The cells were added diluted compound solution (10 uM for top dose), and incubated at 37° C. in 5% $CO_2$ for 72 hours. The number of viable cells was measured using CellTiter-Glo cell viability assay (Promega #G7571). The luminescence signal was read using a ARVO-SX multimode plate reader (Perkin-Elmer). Percent inhibition of cell growth was calculated relative to vehicle treated control wells. Concentration of compound that inhibit 50% of control cell growth (1050) was interpolated using nonlinear regression and the equation;

$$Y = \text{Bottom} + (\text{Top} - \text{Bottom})/(1 + 10\hat{}((\text{Log } ED50 - X)*\text{Hill slope}))$$

X is the logarithm of concentration, Y is the response. Y starts at Bottom and goes to Top with a sigmoid shape.

A 4-fold serial dilution series of Compound A (final 1 uM to 62.5 nM) were prepared. Also, a 2-fold serial dilution series of cytotoxic agents was prepared, in which the starting maximum concentration was fixed as final 160 times of the $IC_{50}$ values determined in single agent titrations for cytotoxic assay described above. Then, Compound A and cytotoxic agents were added to each well and incubated at 37° C. in 5% $CO_2$ for 24 hours. The caspase-3/7 activity within cells was measured by using Caspase-Glo 3/7 Assay (Promega #G8092). Medium was removed and 50 ul of Caspase-Glo reagents were added to wells. The luminescence signal was read using a ARVO-SX multimode plate reader (Perkin-Elmer). Relative Caspase-3/7 induction level was then calculated as the fold increase compared with the level of caspase-3/7 induction in the non-treatment group.

Example 8

TABLE 5

Synergistic effect of the combination Compound A and other standard of care agents (SOCs) on in vitro proliferation/viability of NCI-H460 NSCLC cell line

| Combination partner | Mode of action | Fractional inhibition of proliferation caused by combination of carboplatin and Compound A | | | Caspase-3/7 fold induction at 24 h | | |
|---|---|---|---|---|---|---|---|
| | | $ED_{50}$ Combination index for above | $ED_{75}$ | $ED_{90}$ | (fold of DMSO control) Compound A (nM) | | |
| SOCs | action | fractional inhibition | | | 62.5 | 250 | 1000 |
| Doxorubicin | Topoisomerase inhibitor | 0.27 | 0.18 | 0.17 | 1.3 | 1.7 | 2.8 |
| Campto-thecin | Topoisomerase inhibitor | 0.39 | 0.39 | 0.63 | 1.2 | 1.4 | 1.7 |
| 5-FU | Anti-metabolites | 0.35 | 0.30 | 0.37 | 1.2 | 1.3 | 1.4 |

The relationship between SOC and Compound A concentrations and inhibition of proliferation/viability in H460 cells was measured after simultaneous treatment with both agents for 72 h. The data were analyzed by using CalcuSyn software that calculates the combination index (CI) for each combination of SOCs and Compound A. CI < 0.9 indicates synergism; CI = 0.9 to 1.1 indicates additivity; and CI > 1.1 indicates antagonism. Caspase-3/7 induction was determined by a luminescent assay with luminogenic caspase-3/7 substrate (Caspase-Glo 3/7 assay; Promega).

Materials & Methods

T5.1. Compounds

Compound A was dissolved in dimethyl sulphoxide (DMSO) (SIGMA, #D2650) to make 10 mM stock solution and stored at −20° C. Doxorubicin (SIGMA, #D1515) was dissolved in sterile distilled water and stored at −20° C. Camptothecin (SIGMA, #C9911) was dissolved in DMSO and stored at −20° C. 5-Fluorouracil (5-FU) (SIGMA, #F6627) was dissolved in PBS and stored at −20° C.

T5.2. Cell Lines

Human non-small cell lung cancer cell (NCI-H460) was obtained from the American Type Culture Collection (ATCC). NCI-H460 cells were cultured in RPMI-1640 containing heat-inactivated 10% fetal bovine serum (FBS) in a humidified incubator at 37° C. in 5% $CO_2$.

T5.3. In Vitro Combination of Compound A with Doxorubicin

NCI-H460 NSCLC cell line was seeded at 2,000 cells/well in RPMI 1640 supplemented with 10% heat-inactivated FBS in 96 well tissue culture plates (CORNING #3340) and incubated at 37° C. in 5% $CO_2$ overnight. On the next day Compound A, doxorubicin or the combination of the two agents was added as a 2-fold dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminescence signal was read using a ARVO-SX multimode plate reader (Perkin-Elmer). Combination index was determined by the same method as described in section T1.3.

T5.4. In Vitro Combination of Compound A with Camptothecin

NCI-H460 NSCLC cell line was seeded at 2,000 cells/well in RPMI 1640 supplemented with 10% heat-inactivated FBS in 96 well tissue culture plates (CORNING #3340) and incubated at 37° C. in 5% $CO_2$ overnight. On the next day Compound A, camptothecin or the combination of the two agents was added as a 2-fold dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminescence signal was read using a ARVO-SX multimode plate reader (Perkin-Elmer). Combination index was determined by the same method as described in section T1.3.

T5.5. In Vitro Combination of Compound A with 5-FU

NCI-H460 NSCLC cell line was seeded at 2,000 cells/well in RPMI 1640 supplemented with 10% heat-inactivated FBS in 96 well tissue culture plates (CORNING #3340) and incubated at 37° C. in 5% $CO_2$ overnight. On the next day Compound A, 5-FU or the combination of the two agents was added as a 2-fold dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminescence signal was read using a ARVO-SX multimode plate reader (Perkin-Elmer). Combination index was determined by the same method as described in section T1.3.

T5.6. Caspase-3/7 Assay

Caspase-3/7 assay with NCI-11460 cell line was conducted by the same procedure with section T4.6. as described above.

Example 9

TABLE 6

Synergistic effect of the combination Compound A and erlotinib on in vitro proliferation/viability of NSCLC cell lines

| NSCLC cell line name | Known defects in PI3K or Ras pathway | Fractional inhibition of proliferation caused by combination of Erlotinib and Compound A | | |
|---|---|---|---|---|
| | | $ED_{50}$ | $ED_{75}$ | $ED_{90}$ |
| | | Combination index for above fractional inhibition | | |
| A431 (epidermoid) | EGFR amplification | 0.42 | 0.21 | 0.14 |
| HCC827 | EGFR amplification EGFR E746-750 deletion | 0.39 | 0.18 | 0.12 |
| H292 | Wild type | 0.44 | 0.31 | 0.28 |
| H358 | KRAS G12C | 0.44 | 0.19 | 0.08 |
| H23 | KRAS G12C | 0.32 | 0.46 | 0.68 |
| H1299 | KRAS Q61K | 0.28 | 0.31 | 0.52 |
| Calu-6 | KRAS Q61K | 0.49 | 0.25 | 0.13 |
| H460 | PIK3CA E545K KRAS Q61H | 0.34 | 0.23 | 0.17 |

The fixed ratio experimental design originally described by Chou-Talalay was used. The in vitro anti-proliferative potencies ($IC_{50}$) of erlotinib and Compound A as single agents were first determined separately to yield the $IC_{50 Erlotinib}/IC_{50 Compound\ A}$ ratio. A dilution series of erlotinib/Compound A combinations in which the ratio of [Erlotinib]/[Compound A] was fixed and equal to the $IC_{50 Erlotinib}/IC_{50 Compound\ A}$ ratio was then prepared. Corresponding single agent dilution series of erlotinib and Compound A were also prepared. The three dilution series were tested in the proliferation/viability assay (CellTiter-Glo Luminescent Cell Viability Assay; Promega). The data were analyzed by using CalcuSyn software that calculates the combination index (CI) for each combination of erlotinib/Compound A. CI < 0.9 indicates synergism; CI = 0.9 to 1.1 indicates additivity; and CI > 1.1 indicates antagonism.

Materials & Methods

T6.1. Compounds

Compound A was dissolved in dimethyl sulphoxide (DMSO) (SIGMA, #D2650) to make 10 mM stock solution and stored at −20° C. Erlotinib was dissolved in dimethyl sulphoxide (DMSO) (SIGMA, #D2650) to make 10 mM stock solution and stored at −20° C.

T6.2. Cell Lines

Human epidermoid carcinoma cells (A431), human non-small cell lung cancer cells (HCC827, NCI-H292, NCI-H358, NCI-H23, NCI-H1299, Calu-6, and NCI-H460) were obtained from the American Type Culture Collection (ATCC). All cell lines were cultured in RPMI-1640 containing heat-inactivated 10% fetal bovine serum (FBS) in a humidified incubator at 37° C. in 5% $CO_2$.

T6.3. In Vitro Combination of Compound A with EGFR Inhibitor Erlotinib

Eight NSCLC cell line lines and A431 epidermoid cell line were seeded at 2,000 cells/well in RPMI 1640 supplemented with 10% heat-inactivated FBS in 96 well tissue culture plates (CORNING #3340) and incubated at 37° C. in 5% $CO_2$ overnight. On the next day Compound A, erlotinib or the combination of the two agents were added as a 2-fold dilution series in RPMI containing 1% DMSO. The final DMSO concentration in each assay was 0.1%. The plates were then incubated at 37° C. in 5% $CO_2$ for 72 hours. The number of viable cells was measured using CellTiter-Glo cell viability assay (Promega #G7571). The luminiscence signal was read using a ARVO-SX multimode plate reader (Perkin-Elmer). Combination index was determined by the same method as described in section T1.3.

Example 10

Figure 4:
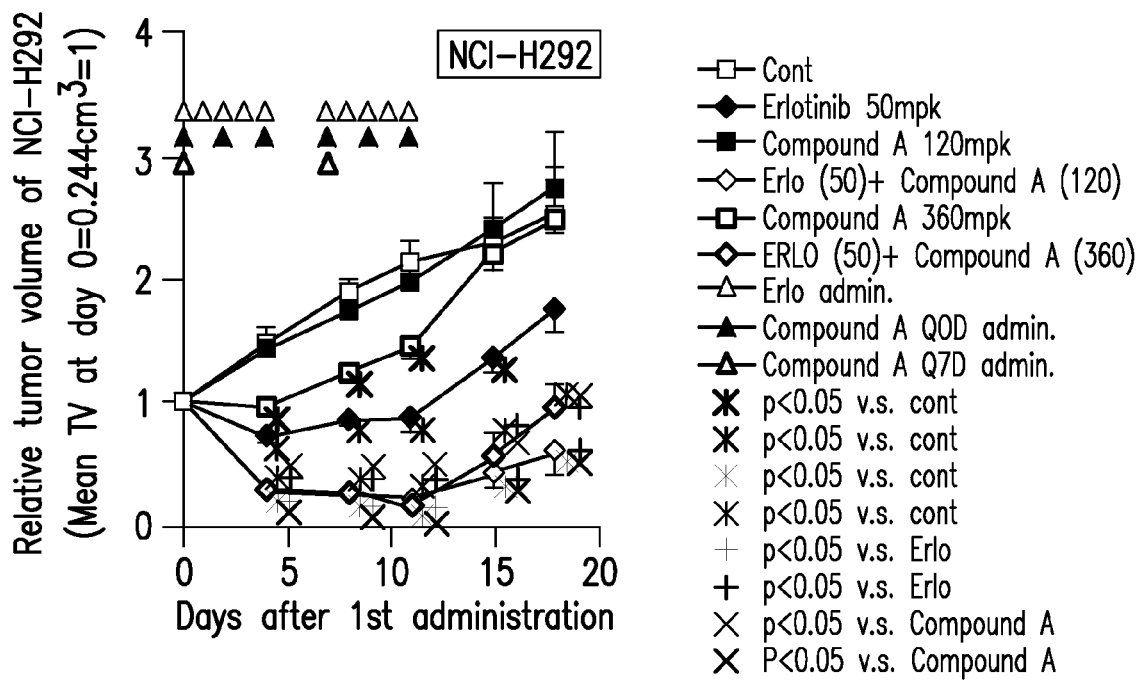
FIG. 4 is a graph that shows an enhanced effect of the combination Compound A and erlotinib on anti-tumor effect in NCI-H292 NSCLC xenograft mice.

Enhanced Effect of the Combination Compound A and Erlotinib on Anti-Tumor Effect in NCI-H292 NSCLC Xenograft Mice (FIG. 4)

Materials & Methods

NCI-H292 NSCLC cell was obtained from the American Type Culture Collection (ATCC). NCI-H292 cells were cultured in RPMI-1640 containing heat-inactivated 10% fetal bovine serum (FBS) in a humidified incubator at 37° C. in 5% $CO_2$. These cells were suspended in 50% Matrigel (BD Biosciences) diluted with PBS, and were subcutaneously transplanted into side flank of CD1-nude mice by using needle and syringe ($1 \times 10^7$ NCI-H292 cells/100 μL,) under isoflurane anesthesia. Mice were randomized according to NCI-H292 tumor volumes and distributed into treatment groups of 5 mice with approximately equivalent ranges of tumor volumes between treatment groups.

Compound A was dissolved in 30% captisol (Cydex). Erlotinib was suspended in 0.5% methylcellulose (MC)+0.1% Tween 80. On 13th day post-tumor transplantation, vehicle (0.5% MC+0.1% Tween 80) or erlotinib at 50 mg/kg was administered orally once per day for 5 days during two weeks. Compound A at 120 mg/kg was administered orally three times per week for two weeks and Compound A at 360 mg/kg was administered once per week for two weeks. For combination group, anti-tumor efficacy in two regimens was compared between erlotinib+Compound A at 120 mg/kg (three times per week) or erlotinib+Compound A at 360 mg/kg (once per week).

Measurement of tumor volume, body weight and gross observation were performed. Tumor volume was determined by measuring tumor diameters with digital caliper at the day 0, 4, 7, 11, and 18. Measurement of body weight and gross observation were performed every week day during the experiment. Anti-tumor efficacy was monitored by the same method as described in section FIG. 1.

Example 11

TABLE 7

Synergistic effect of the combination Compound A and lapatinib on in vitro proliferation/viability of breast cancer cell lines

| Breast cancer cell line name | Known defects in PI3K pathway | Known RTK defects | Fractional inhibition of proliferation caused by combination of lapatinib and Compound A | | |
|---|---|---|---|---|---|
| | | | $ED_{50}$ | $ED_{75}$ | $ED_{90}$ |
| | | | Combination index for above fractional inhibition | | |
| BT20 | PIK3CA H1047/P539R | EGFR overexpression | 0.7 | 0.6 | 0.5 |
| BT-474 | PIK3CA K111N | Her2 amp | 0.8 | 0.9 | 1.1 |
| HCC 1569 | PTEN 267fs*9 | | 0.3 | 0.4 | 0.6 |
| HCC 1937 | PTEN null | | 0.4 | 0.3 | 0.2 |
| HCC70 | PTEN 90fs*9 | | 0.6 | 0.5 | 0.5 |
| MCF-7 | PIK3CA E545K | | 0.6 | 0.5 | 0.4 |
| MDA-MB-453 | PIK3CA H1047/PTEN E307K | Her2 amp | 0.4 | 0.3 | 0.3 |
| MDA-MB-468 | PTEN a72fsx5 | EGFR overexpression | 0.8 | 0.5 | 0.4 |

The fixed ratio experimental design described originally by Chou-Talalay was used. The in vitro anti-proliferative potencies ($IC_{50}$) of lapatinib and Compound A as single agents were first determined separately to yield $IC_{50 lapatinib}/IC_{50 Compound A}$ ratio. A dilution series of lapatinib/Compound A combinations was then prepared in which the ratio of [lapatinib]/[Compound A] was fixed and equal to the $IC_{50 lapatinib}/IC_{50 Compound A}$ ratio described above. Corresponding single agent dilution series of lapatinib and Compound A were also prepared. The three dilution series were then tested in the proliferation/viability assay (Vialight). The data were analyzed using CalcuSyn software that calculates combination index (CI) for each combination of lapatinib/Compound A. CI < 0.9 indicates synergism; CI = 0.9 to 1.1 indicates additivity and CI > 1.1 indicates antagonism.

Materials & Methods

T7.1. Compounds

Compound A was dissolved in dimethyl sulphoxide (DMSO) (SIGMA, #D2650) to make 10 mM stock solution and stored at −20° C. Lapatinib was dissolved in dimethyl sulphoxide (DMSO) (SIGMA, #D2650) to make 10 mM stock solution and stored at −20° C.

T7.2. Cell Lines

Human breast cancer cell lines (BT-20, BT-474, HCC1569, HCC1937, HCC70, MCF-7, MDA-MB-453, and MDA-MB-468) were obtained from the American Type Culture Collection (ATCC). All cell lines were cultured in RPMI-1640 containing heat-inactivated 10% fetal bovine serum (FBS) in a humidified incubator at 37° C. in 5% $CO_2$.

T7.3. In Vitro Combination of Compound A with EGFR/HER2 Inhibitor Lapatinib

All breast cancer cell lines (total 8 cell lines) were seeded at 3,000 cells/well in RPMI 1640 supplemented with 10% heat-inactivated FBS in 96 well tissue culture plates (CORNING #3340) and incubated at 37° C. in 5% $CO_2$ overnight. On the next day Compound A, lapatinib or the combination of the two agents was added as a dilution series in RPMI containing 5% DMSO. The final DMSO concentration in each assay was 0.1%. The plates were then incubated at 37° C. in 5% $CO_2$ for 72-96 hours. The number of viable cells was measured using ATPlite Luminescence Assay System (Perkin-Elmer #6016949). The luminiscence signal was read using a Victor3 multimode plate reader (Perkin-Elmer). Combination index was determined by the same method as described in section T1.3.

Example 12

Figure 5:
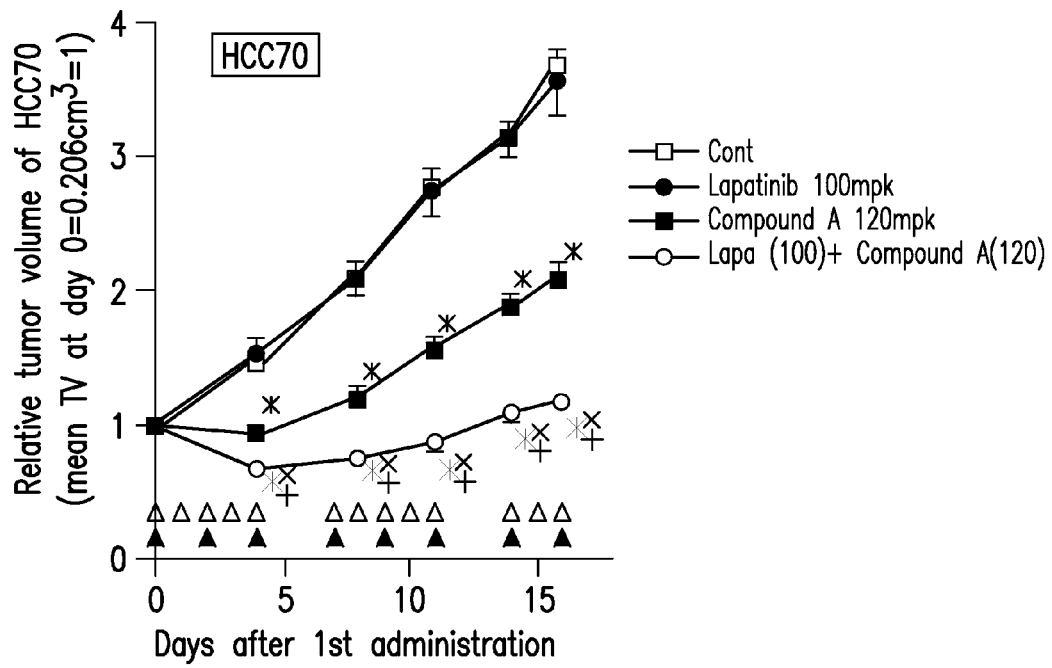
FIG. 5 is a graph that shows an enhanced effect of the combination Compound A and lapatinib on anti-tumor effect in HCC70 breast xenograft mice.

Enhanced Effect of the Combination Compound A and Lapatinib on Anti-Tumor Effect in HCC70 Breast Xenograft Mice (FIG. 5)

Materials & Methods

HCC70 human breast cancer cell was obtained from the American Type Culture Collection (ATCC). HCC70 cells were cultured in RPMI-1640 containing heat-inactivated 10% fetal bovine serum (FBS) in a humidified incubator at 37° C. in 5% $CO_2$, These cells were suspended in 50% Matrigel (BD Biosciences) diluted with PBS, and were subcutaneously transplanted into side flank of scid mice by using needle and syringe ($1 \times 10^7$ HCC70 cells/100 µL,) under isoflurane anesthesia. Mice were randomized according to HCC70 tumor volumes and distributed into treatment groups of 5 mice with approximately equivalent ranges of tumor volumes between treatment groups.

Compound A was dissolved in 30% captisol (Cydex). Lapatinib was suspended in saline. On 16th day post-tumor transplantation, vehicle (saline) or lapatinib at 100 mg/kg was administered orally once per day for 5 days during two weeks and additional 3 days at third cycle. Compound A at 120 mg/kg was administered orally three times per week for two weeks and additional 2 days at third cycle. For combination group, anti-tumor efficacy in two regimens was compared between lapatinib at 100 mg/kg+Compound A at 120 mg/kg (three times per week). Measurement of tumor volume, body weight and gross observation were performed. Tumor volume was determined by measuring tumor diameters with digital caliper at the day 0, 4, 8, 11, 14 and 16. Measurement of body weight and gross observation were performed every week day during the experiment. Anti-tumor efficacy was monitored by the same method as described in section FIG. 1. Statically significance for tumor volume was determined by repeated measure. ANOVA followed by Dunnett test (*: p<0.05 vs control) and unpaired t-test (+: p<0.05 vs lapatinib).

Example 13

Figure 6:
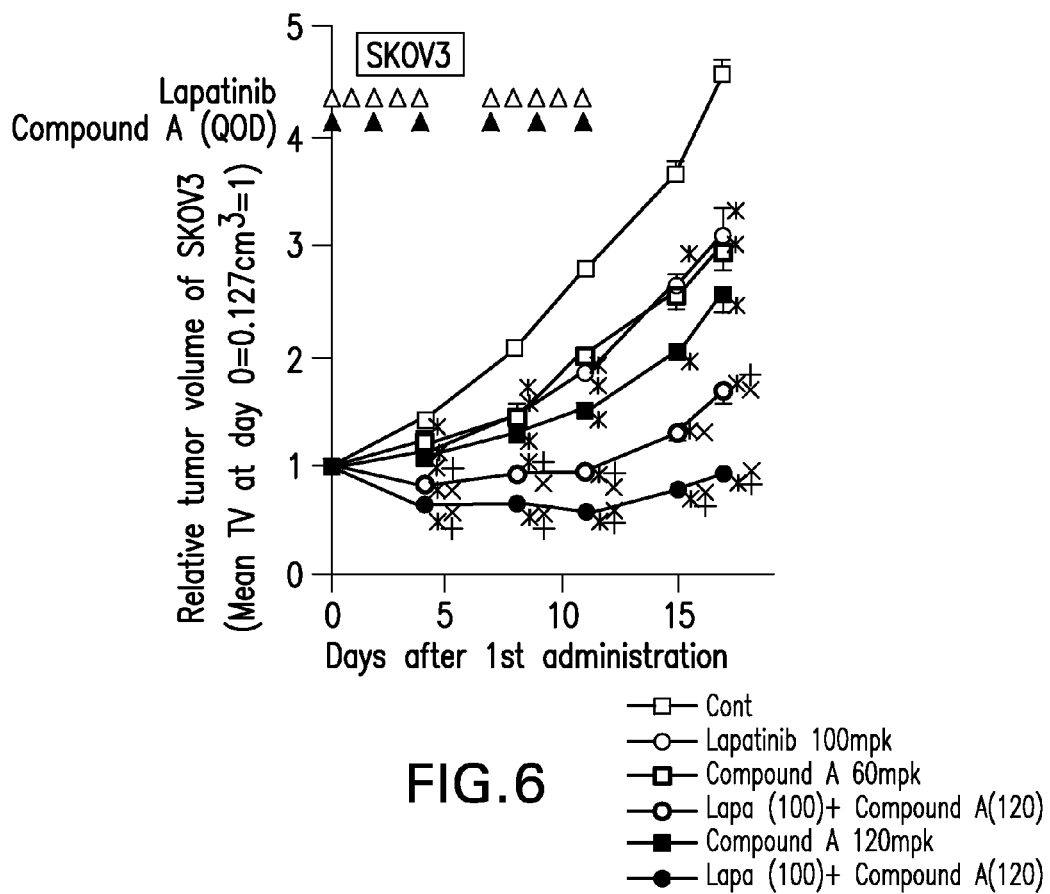
FIG. 6 is a graph that shows an enhanced effect of the combination Compound A and lapatinib on anti-tumor effect in SK-OV-3 ovarian xenograft mice.

Enhanced Effect of the Combination Compound A and Lapatinib on Anti-Tumor Effect in SK-OV-3 Ovarian Xenograft Mice (FIG. 6)

Materials & Methods

SK-OV-3 human ovarian cancer cell was obtained from the American Type Culture Collection (ATCC). SK-OV-3 cells were cultured in RPMI-1640 medium containing heat-inactivated 10% fetal bovine serum (FBS) in a humidified incubator at 37° C. in 5% $CO_2$. These cells were suspended in 50% Matrigel (BD Biosciences) diluted with PBS, and were subcutaneously transplanted into side flank of scid mice by using needle and syringe ($1\times10^7$ SK-OV-3 cells/100 μL,) under isoflurane anesthesia. Mice were randomized according to SK-OV-3 tumor volumes and distributed into treatment groups of 5 mice with approximately equivalent ranges of tumor volumes between treatment groups.

Compound A was dissolved in 30% captisol (Cydex). Lapatinib was suspended in distilled water. On 18th day post-tumor transplantation, vehicle (distilled water) or lapatinib at 100 mg/kg was administered orally once per day for 5 days during two weeks. Compound A at 60 and 120 mg/kg was administered orally three times per week for two weeks. For combination group, anti-tumor efficacy in two regimens was compared between lapatinib at 100 mg/kg+Compound A at 60 or 120 mg/kg (three times per week).

Measurement of tumor volume, body weight and gross observation were performed. Tumor volume was determined by measuring tumor diameters with digital caliper at the day 0, 4, 8, 11, and 17. Measurement of body weight and gross observation were performed every week day during the experiment. Anti-tumor efficacy was monitored by the same method as described in section FIG. 1. Statically significance for tumor volume was determined by repeated measure. ANOVA followed by Dunnett test (*: $p<0.05$ vs control), (+: $p<0.05$ vs lapatinib).

The invention claimed is:

1. A combined anticancer agent for simultaneous, separate or successive administration in cancer therapy, comprising the following pharmaceutical preparations (a) and (b):
   (a) a pharmaceutical preparation comprising 8-[4-(1-aminocyclobutyl)phenyl]-9phenyl[1,2,4]triazolo[3,4-f]-1,6-naphthyridin-3(2H)-one or a pharmaceutically acceptable salt thereof, together with a pharmaceutically acceptable carrier or diluent, and
   (b) a pharmaceutical preparation comprising, together with a pharmaceutically acceptable carrier or diluent, at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, or a pharmaceutically acceptable salt thereof, wherein
      the anticancer antimetabolites are 5-fluorouracil and gemcitabine;
      the anticancer antibiotics is doxorubicin;
      the plant-derived anticancer agents are docetaxel and paclitaxel;
      the anticancer platinum-coordinated complex compounds are cisplatin and carboplatin;
      the anticancer camptothecin derivatives is camptothecin; and
      the anticancer tyrosine kinase inhibitors are lapatinib and erlotinib and wherein
      the cancer is selected from breast cancer, endometrial cancer, non-small cell lung cancer, ovarian cancer and prostate cancer.

2. An anticancer agent comprising 8-[4-(1-aminocyclobutyl)phenyl]-9-phenyl[1,2,4]triazolo[3,4-f]-1,6-naphthyridin-3(2H)-one or a pharmaceutically acceptable salt thereof, and at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as defined in claim 1, or a pharmaceutically acceptable salt thereof, together with a pharmaceutically acceptable carrier or diluent.

3. A pharmaceutical kit comprising in a first compartment 8-[4-(1-aminocyclobutyl)phenyl]-9-phenyl[1,2,4]triazolo[3,4-f]-1,6-naphthyridin-3(2H)-one or a pharmaceutically acceptable salt thereof together with a pharmaceutically acceptable carrier or diluent, and in a second compartment at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as defined in claim 1, or a pharmaceutically acceptable salt thereof, together with a pharmaceutically acceptable carrier or diluent.

4. A method for the treatment of cancer, which comprises administering to a subject in need thereof a therapeutically-effective amount of 8-[4-(1-aminocyclobutyl)phenyl]-9-phenyl[1,2,4]triazolo[3,4-f]-1,6-naphthyridin-3(2H)-one or a pharmaceutically acceptable salt thereof, in combination with at least one anticancer agent selected from the group consisting of anticancer antimetabolites, anticancer antibiotics, plant-derived anticancer agents, anticancer platinum-coordinated complex compounds, anticancer camptothecin derivatives and anticancer tyrosine kinase inhibitors, wherein the definition of each anticancer agent is the same as defined in claim 1, or a pharmaceutically acceptable salt thereof.

5. The method according to claim 4, wherein the cancer is selected from breast cancer, endometrial cancer, non-small cell lung cancer, ovarian cancer and prostate cancer.

* * * * *